United States Patent
Sugiura

(10) Patent No.: US 9,624,462 B2
(45) Date of Patent: Apr. 18, 2017

(54) CELL SEPARATION CONTAINER

(71) Applicant: JAPAN TISSUE ENGINEERING CO., LTD., Gamagori-shi, Aichi (JP)

(72) Inventor: Makoto Sugiura, Gifu (JP)

(73) Assignee: JAPAN TISSUE ENGINEERING CO, LTD., Aichi (JP)

( * ) Notice: Subject to any disclaimer, the term of this patent is extended or adjusted under 35 U.S.C. 154(b) by 72 days.

(21) Appl. No.: 14/367,063

(22) PCT Filed: Dec. 25, 2012

(86) PCT No.: PCT/JP2012/083462
§ 371 (c)(1),
(2) Date: Jun. 19, 2014

(87) PCT Pub. No.: WO2013/103108
PCT Pub. Date: Jul. 11, 2013

(65) Prior Publication Data
US 2014/0356939 A1 Dec. 4, 2014

(30) Foreign Application Priority Data

Jan. 4, 2012 (JP) .................................. 2012-000138

(51) Int. Cl.
*C12M 1/00* (2006.01)
*C12M 3/00* (2006.01)

(52) U.S. Cl.
CPC ............ *C12M 47/04* (2013.01); *C12M 45/06* (2013.01); *C12M 45/09* (2013.01); *C12M 47/02* (2013.01)

(58) Field of Classification Search
CPC ...... C12M 21/08; C12M 25/02; C12M 29/04; C12M 33/14; C12M 47/02
See application file for complete search history.

(56) References Cited

U.S. PATENT DOCUMENTS 5,624,418 A * 4/1997 Shepard .............. A61M 1/0056
210/232
5,888,409 A 3/1999 Morsiani et al.
(Continued)

FOREIGN PATENT DOCUMENTS

CN 102120111 A 7/2011
CN 102212461 A 10/2011
(Continued)

OTHER PUBLICATIONS

Huang et al., "A Tunable Micro Filter Modulated by Pneumatic Pressure for Cell Separation," *Sensors and Actuators B: Chemical*, 2009, vol. 142. pp. 389-399.
(Continued)

*Primary Examiner* — Nathan Bowers
(74) *Attorney, Agent, or Firm* — Oliff PLC

(57) ABSTRACT

A cell separation container includes a collection chamber and a tissue holding chamber which are partitioned by a filter. The cell separation container includes a first air pressure adjuster configured to adjust the inflow and outflow of gas in the collection chamber and a second air pressure adjuster configured to adjust the inflow and outflow of gas in the tissue holding chamber. Thus, the inflow and outflow of the outside air and the gases in the collection chamber and the tissue holding chamber can be adjusted. In the cell separation container, switching between holding a treatment liquid in the tissue holding chamber and ejecting a treatment liquid to the collection chamber can be performed by adjusting the inflow and outflow of the outside air and the gas in the connection chamber.

15 Claims, 12 Drawing Sheets

(56) References Cited

U.S. PATENT DOCUMENTS

| | | | |
|---|---|---|---|
| 5,968,356 A | 10/1999 | Morsiani et al. | |
| 8,366,694 B1* | 2/2013 | Jordan | A61M 1/0001 604/19 |
| 2007/0298451 A1 | 12/2007 | Ribault et al. | |
| 2008/0199900 A1 | 8/2008 | Signore et al. | |
| 2009/0181450 A1 | 7/2009 | Ribault et al. | |

FOREIGN PATENT DOCUMENTS

| | | |
|---|---|---|
| JP | A-2001-525686 | 12/2001 |
| JP | A-2008-5840 | 1/2008 |
| JP | A-2009-38998 | 2/2009 |
| JP | 2009-095307 A | 5/2009 |
| JP | B2-4520855 | 8/2010 |
| WO | WO 2011/117821 A1 | 9/2011 |

OTHER PUBLICATIONS

International Search Report issued in International Application No. PCT/JP2012/083462 mailed Mar. 12, 2013.
Sep. 11, 2015 Extend Search Report issued in European Patent Application No. 12864255.0.
International Preliminary Report on Patentability issued in International Application No. PCT/JP2012/083462 dated Jul. 8, 2014.
Jan. 27, 2015 Office Action issued in Chinese Application No. 201280066057.0.

\* cited by examiner

CELL SEPARATION CONTAINER

TECHNICAL FIELD

The present invention relates to a cell separation container.

BACKGROUND ART

In recent years, cell culture techniques have been used in various fields. For example, cells are cultured in vitro and the cultured cells are administered to patients in a treatment or are used in toxicity tests for drugs and the like. Such cell culture techniques have been used for a long time, but most of cell culture processes have involved manual operations, which impose a heavy burden on workers. Therefore, it is desirable to simplify or automate each operation. In particular, in an initial process of cell culture in which a cell is separated from a body tissue, many operations need to be performed, such as washing and disinfecting a body tissue biopsied from a patient or donor and separating a cell from the body tissue by performing a treatment with an enzyme-containing liquid. This imposes a heavy burden on workers.

For example, PTL 1 discloses a cell dispersion device including a tissue holding member that can hold a body tissue and at least partly has a plurality of cell-passing pores with a size at which a cell can be passed; a liquid storage member that can store a dispersant-containing liquid used to immerse the body tissue held in the tissue holding member, the liquid storage member being disposed so as to surround the tissue holding member; and a stream generating member that generates a stream on the dispersant-containing liquid so that the cell separated from the body tissue by the action of the dispersant-containing liquid stored in the liquid storage member passes through the cell-passing pores of the tissue holding member toward the outside of the tissue holding member. A process of separating a cell from a body tissue and dispersing the cell, which has been manually performed, can be automatically conducted by using the cell dispersion device. Therefore, a process of separating a cell from a body tissue and dispersing the cell using a dispersant can be easily conducted.

PTL 1: Japanese Patent No. 4520855

DISCLOSURE OF INVENTION

However, the above-described device requires a large amount of dispersant-containing liquid because a sufficient amount of dispersant-containing liquid needs to be stored for treatment not only in the tissue holding member in which a cell dispersion treatment is performed but also in the liquid storage member. Therefore, the efficiency of the cell dispersion device is not high.

In view of the foregoing, it is a main object of the present invention to provide a cell separation container with which a series of operations for separating a cell by treating a tissue with a treatment liquid can be easily performed efficiently. It is also an object of the present invention to provide a structure that easily allows a cell separation treatment even in a manual operation.

In order to achieve the above main object, the cell separation container of the present invention is constructed as follows.

The cell separation container of the present invention separates a cell from a tissue using a treatment liquid and includes:

a collection chamber for collecting at least one of the treatment liquid and the cell;

a tissue holding chamber disposed above the collection chamber and including a pouring inlet through which the treatment liquid is poured;

a filter disposed as the entirety or part of a structure for partitioning the collection chamber and the tissue holding chamber from each other, the filter being capable of holding the tissue and allowing the cell to pass therethrough; and an air pressure adjusting mechanism capable of switching between a process of holding a treatment liquid poured into the tissue holding chamber without causing the treatment liquid to pass through the filter and a process of ejecting a treatment liquid poured into the tissue holding chamber to the collection chamber by causing the treatment liquid to pass through the filter, the switching being achieved by adjusting inflow and outflow of gases in the collection chamber and the tissue holding chamber.

In the cell separation container, when the tissue is treated in the tissue holding chamber, the treatment liquid can be held in the tissue holding chamber by adjusting the inflow and outflow of gases in the collection chamber and the tissue holding chamber. In addition, when the treatment with the treatment liquid is completed, the treatment liquid and the cell can be easily ejected to the collection chamber while the tissue and a residue are held in the tissue holding chamber. As described above, a series of operations for treating a tissue with a treatment liquid and ejecting the treatment liquid after the treatment can be easily performed efficiently in a minimum amount of the treatment liquid.

The tissue is preferably an epithelial tissue, a connective tissue, a muscular tissue, a nervous tissue, or the like that can be biopsied from a body. Specific examples of the tissue include a portion of tissues such as skin (epidermis or dermis), cartilage, cornea, retina, periosteum, bone, nerve, muscle, mucous membrane, periodontium, blood vessel, and fat; and a portion of organs such as heart, liver, pancreas, kidney, and urinary bladder. Furthermore, a cell mass composed of one or more types of cells, such as a cell sheet or a cell spheroid obtained by culturing a cell or a cultured tissue obtained by disseminating a cell in a scaffold can also be used as the tissue in the present invention.

The treatment liquid is, for example, a transport liquid used to transport a tissue, a disinfectant liquid used to disinfect the tissue, a washing liquid used to wash the tissue, an enzyme solution used to separate a cell from the tissue, or a culture medium. Examples of the transport liquid include a phosphate buffer solution (PBS), a Ringer's solution, and a culture medium. Examples of the washing liquid include a phosphate buffer solution (PBS), a Ringer's solution, and a physiological saline solution. Examples of the disinfectant liquid include alcohols and a povidone-iodine solution. Examples of the enzyme solution include proteases such as trypsin, dispase, collagenase, and gelatinase; peptidases; and glycolytic enzymes. Examples of the culture medium include liquid culture media such as DMEM (Dulbecco's modified eagle medium), α-MEM, and serum-free culture media. The culture medium may contain serums such as FBS (fetal bovine serum), antibiotics such as penicillin and streptomycin, growth factors, and additive substances such as ascorbic acid.

In the cell separation container of the present invention, the air pressure adjusting mechanism may include a first air pressure adjuster configured to adjust inflow and outflow of the gas in the collection chamber, the first air pressure adjuster being disposed in the collection chamber, and a second air pressure adjuster configured to adjust inflow and outflow of the gas in the tissue holding chamber, the second air pressure adjuster being disposed in the tissue holding chamber. Since the air pressure in the collection chamber and the air pressure in the tissue holding chamber can be separately adjusted, the air pressure can be easily adjusted.

In the cell separation container, the first air pressure adjuster may allow circulation of the gas in the collection chamber and outside air and interruption of the circulation, and the second air pressure adjuster may always allow circulation of the gas in the tissue holding chamber and the outside air. Also in this structure, the holding and ejecting of the treatment liquid in the collection chamber and the tissue holding chamber can be controlled. Specifically, when the circulation of the gas in the collection chamber and the outside air is interrupted by the first air pressure adjuster, the treatment liquid poured into the tissue holding chamber serves as a lid to provide a hermetically sealed collection chamber and thus the gas in the collection chamber is held in the collection chamber without causing volume change. Herein, an upward force (hereafter also referred to as an upward supporting force) that is generated by the surface tension and the pressure of the gas in the collection chamber is exerted on the treatment liquid, the upward force being balanced by a downward force generated by gravity and the pressure of the gas in the tissue holding chamber. As a result of the air pressure equilibrium, the treatment liquid can be held in the tissue holding chamber. In order for the treatment liquid to serve as a lid, it is sufficient that the relationship between the surface tension of the treatment liquid and the pore size of the filter be set so that the gas in the collection chamber cannot easily move through the pores of the filter under the pressure of the gas in the collection chamber. However, it is expected that a sufficient effect can be produced as long as the pore size at which the tissue can be held and the cell can be passed is employed. In such a state, the gas in the collection chamber does not move to the tissue holding chamber side, regardless of the circulation of the gas in the tissue holding chamber and the outside air or the interruption of the circulation. Therefore, the upward supporting force is maintained and the treatment liquid can be held in the tissue holding chamber. Subsequently, when the gas in the collection chamber and the outside air are circulated by the first air pressure adjuster, the gas in the collection chamber can flow out. This decreases the upward supporting force and the treatment liquid is ejected to the collection chamber by gravity. As described above, when the first air pressure adjuster is in a state of allowing the interruption of gas circulation, the treatment liquid can be held in the tissue holding chamber by a force generated by air pressure of the collection chamber. When the first air pressure adjuster is in a state of allowing gas circulation, the treatment liquid can be easily ejected to the collection chamber. If the air pressure in the collection chamber is decreased so as to be lower than the air pressure in the tissue holding chamber by, for example, more actively aspirating the gas in the collection chamber using the first air pressure adjuster, the treatment liquid can be ejected more efficiently. This is more effective when the pore size is small and thus the treatment liquid is not easily ejected. Unlike the above-described structure, if the first air pressure adjuster always allows circulation of the gas in the collection chamber and the outside air and the second air pressure adjuster allows circulation of the gas in the tissue holding chamber and the outside air and interruption of the circulation, the same effects will be produced.

The cell separation container of the present invention may include a lower container having an opening in an upper portion thereof; an upper container having an opening in an upper portion thereof, including the filter in a bottom portion thereof, and connected to the lower container in a lower portion thereof; and a lid body attachable to the upper container so as to cover the opening of the upper container, wherein a region surrounded by the lower container and the bottom portion of the upper container may serve as the collection chamber, and a region surrounded by the upper container and the lid body may serve as the tissue holding chamber. In the cell separation container including the lower container, the upper container, and the lid body, the upper container may include an outer frame body having openings in upper and lower portions thereof and connected to the lower container in a lower portion thereof and an incorporation body including the filter and detachably incorporated into the outer frame body, or the upper container may be integrally formed. When the upper container includes the outer frame body and the incorporation body, a desired operation can be performed by changing the combination of the outer frame body and the incorporation body. When the upper container is integrally formed, the upper container is easily handled because of a small number of parts. In the cell separation container including the lower container, the upper container, and the lid body, the lower container may have a structure to which the lid body is attachable. In this case, after the completion of cell separation, the upper container is detached and the lid body is directly attached to the lower container, which allows the subsequent operations and storage to be performed in a compact manner. The lower container, the upper container, and the filter may be integrally formed.

In the cell separation container including the lower container, the upper container, and the lid body, the first air pressure adjuster may include a sealing member disposed in the lid body and a cylindrical member connected to the sealing member and penetrating through the upper container in a vertical direction. The air pressure can be adjusted by the sealing member disposed in the lid body, which simplifies the operation. In such a cell separation container, the first air pressure adjuster may include an aspirating tube that extends from the cylindrical member and reaches a bottom portion of the lower container. When the treatment liquid and the cell collected in the collection chamber are ejected, for example, an operation for inserting an aspirator into the lower container so as to reach the bottom portion can be omitted, which simplifies the operation. This is also suitable for automation.

In the cell separation container including the lower container, the upper container, and the lid body, the lid body may include a lid main body that can be attached to and detached from the upper container by screwing and a rubber layer disposed inside the lid main body, and a rubber hardness of a surface of the rubber layer that is in contact with the lid main body may be higher than that of a surface of the rubber layer that is in contact with the upper container. In this case, a friction is not easily produced between the rubber layer and the lid main body and thus the rubber layer is easily brought into close contact with the upper container. Therefore, when the lid body is attached to the upper container, the rubber layer is not easily twisted and thus the lid is not easily unscrewed. Consequently, the air tightness of the outer container can be further improved.

Alternatively, the cell separation container of the present invention may include an outer container having an opening in an upper portion thereof; an inner container incorporated into an upper portion of the outer container, having an opening in an upper portion thereof, and including the filter in a bottom portion thereof; and a lid body attachable to the outer container into which the inner container has been incorporated, wherein a region surrounded by the outer container and the lid body and located outside the inner container may serve as the collection chamber, and a region surrounded by the inner container and the lid body may serve as the tissue holding chamber. Such a cell separation container has high versatility because a commercially available centrifuge tube or the like can be applied to the outer container and the lid body.

In the cell separation container including the outer container, the inner container, and the lid body, the first air pressure adjuster may include a sealing member disposed in the lid body and a cylindrical member connected to the sealing member and penetrating through the inner container in a vertical direction. The air pressure can be adjusted by the sealing member disposed in the lid body, which simplifies the operation. In such a cell separation container, the first air pressure adjuster may include an aspirating tube that extends from the cylindrical member and reaches a bottom portion of the outer container. When the treatment liquid and the cell collected in the collection chamber are ejected, for example, an operation for inserting an aspirator so as to reach the bottom portion of the outer container can be omitted, which simplifies the operation. This is also suitable for automation.

In the cell separation container including the outer container, the inner container, and the lid body, the lid body may include a lid main body that can be attached to and detached from the outer container by screwing and a rubber layer disposed inside the lid main body, and a rubber hardness of a surface of the rubber layer that is in contact with the lid main body may be higher than that of a surface of the rubber layer that is in contact with the outer container and/or the inner container. In this case, a friction is not easily produced between the rubber layer and the lid main body and thus the rubber layer is easily brought into close contact with the outer container and the inner container. Therefore, when the lid body is attached to the outer container, the rubber layer is not easily twisted and thus the lid is not easily unscrewed. Consequently, the air tightness of the outer container and the inner container can be further improved.

BEST MODES FOR CARRYING OUT THE INVENTION

Preferred embodiments of the present invention will now be described with reference to the attached drawings.

First Embodiment

Figure 1:
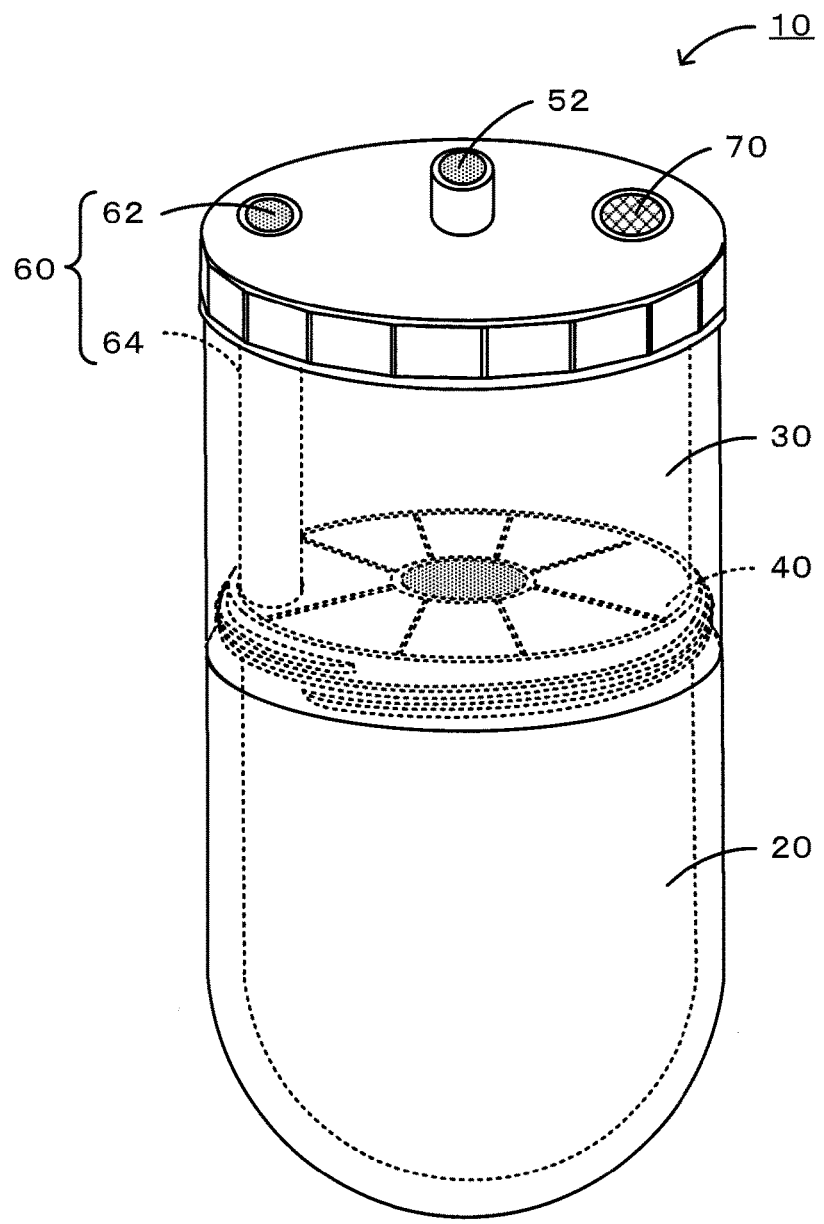
FIG. 1 is a perspective view of a cell separation container 10 according to a first embodiment.
Figure 2:
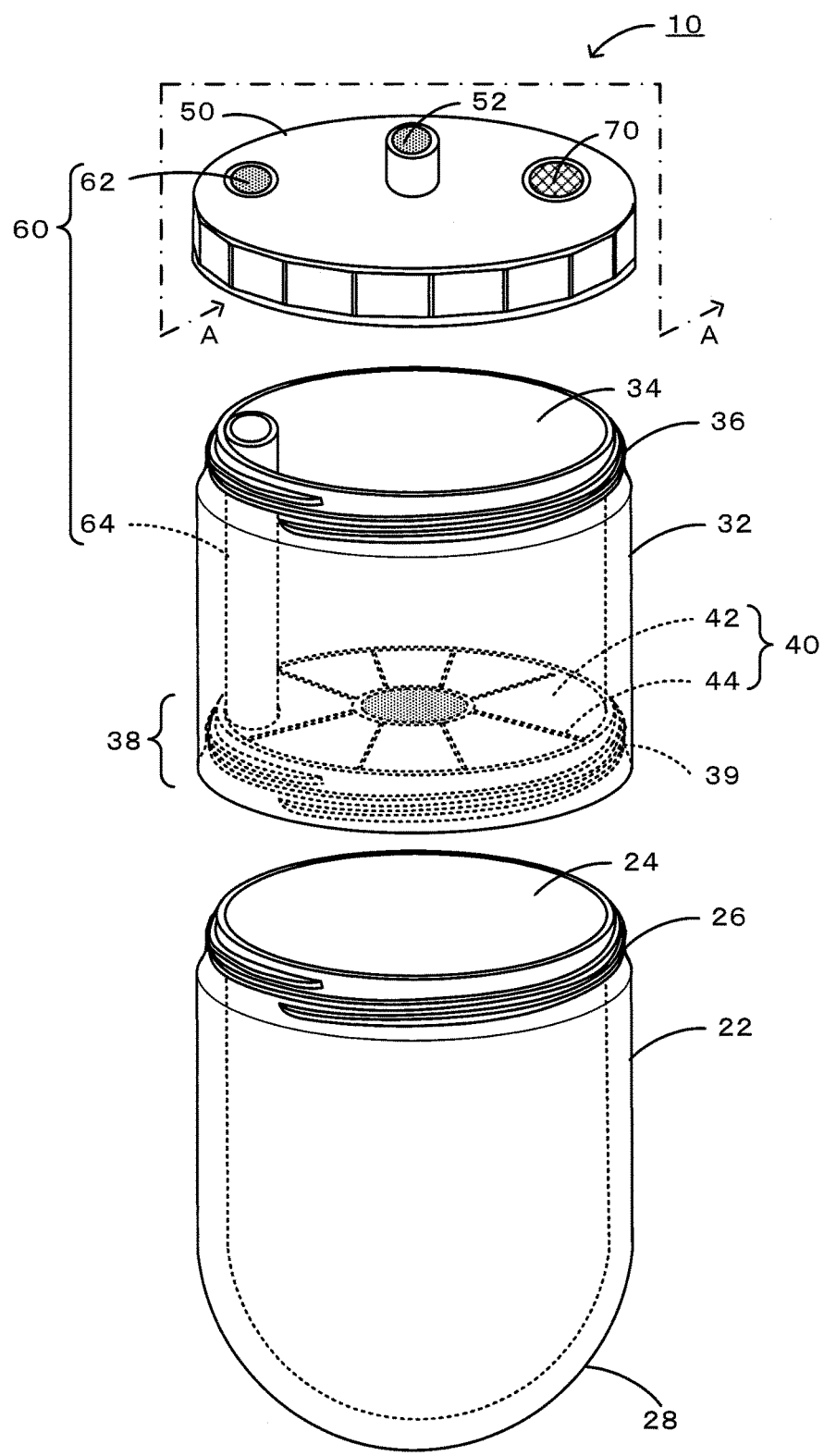
FIG. 2 is a perspective view of the cell separation container 10 before assembling.
Figure 3:
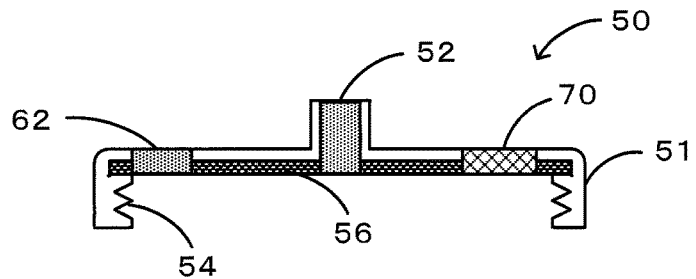
FIG. 3 is a schematic sectional view taken along line A-A in FIG. 2.

FIG. 1 is a perspective view of a cell separation container 10 according to a first embodiment. FIG. 2 is a perspective view of the cell separation container 10 before assembling. FIG. 3 is a schematic sectional view taken along line A-A in FIG. 2.

As shown in FIG. 1, the cell separation container 10 includes a collection chamber 20 and a tissue holding chamber 30 which are partitioned by a filter 40. The cell separation container 10 includes a first air pressure adjuster 60 configured to adjust the inflow and outflow of gas in the collection chamber 20 and a second air pressure adjuster 70 configured to adjust the inflow and outflow of gas in the tissue holding chamber 30. Thus, the inflow and outflow of the outside air and the gases in the collection chamber 20 and the tissue holding chamber 30 can be adjusted. As shown in FIG. 2, the cell separation container 10 includes a lower container 22, an upper container 32 including the filter 40, and a lid body 50 attachable to the upper container 32 so as to cover an opening 34 of the upper container 32. A region surrounded by the lower container 22 and a bottom portion 38 of the upper container 32 serves as the collection chamber 20. A region surrounded by the upper container 32 and the lid body 50 serves as the tissue holding chamber 30.

The lower container 22 has a cylindrical shape with a bottom and a bottom portion 28 has a curved surface that smoothly extends from a side wall. The bottom portion 28 may have a conical shape whose surface smoothly extends from a side wall. In this case, a cell is easily accumulated (cell pellet is easily formed) in the bottom portion 28 when the cell separation container 10 is subjected to centrifugal separation after the cell separation. The lower container 22 has an opening 24 in an upper portion thereof, and an external thread 26 is disposed on the peripheral side of the opening.

The upper container 32 has a cylindrical shape and includes an internal thread 39 on the internal circumference in the bottom portion thereof. The internal thread 39 and the external thread 26 of the lower container 22 are screwed so that the upper container 32 and the lower container 22 are connected to each other. The upper container 32 has an opening 34 in an upper portion thereof, and an external thread 36 is disposed on the peripheral side of the opening.

The filter 40 is heat-welded to a portion above an internal thread 39 which is located in the bottom portion 38 of the upper container 32. The filter 40 includes a filter member 42 and a frame 44 for fixing the filter member 42 to the upper container 32. The frame 44 is constituted by a disc-shaped part disposed in the center, a ring-shaped part disposed along the internal circumference of the upper container 32, and eight beams that connect the disc-shaped part and the ring-shaped part. The filter member 42 is stretched in the frame 44. The shape and form of the frame 44 may be appropriately designed. The entirety of the filter 40 may be constituted by the filter member 42, but strength can be provided by employing the above-described structure. The filter member 42 may be any filter member that can hold a tissue and can pass a cell, but is preferably a membrane filter. Such a membrane filter is composed of nylon (registered trademark), polytetrafluoroethylene (PTFE), cellulose, or the like. The pore size of the filter member 42 may be appropriately set in consideration of, for example, the surface tension (viscosity) of a treatment liquid so that gas in the collection chamber cannot easily move to the tissue holding chamber through filter pores under a predetermined air pressure condition as described above. For example, the pore size is preferably 30 μm or more and 100 μm or less and more preferably 40 μm or more and 70 μm or less.

As shown in FIG. 3, the lid body 50 includes an internal thread 54 on the internal circumference thereof. The internal thread 54 and the external thread 36 of the upper container 32 are screwed so that the lid body 50 and the upper container 32 are connected to each other. The internal thread 54 can also be screwed onto the external thread 26 of the lower container 22. Therefore, the lid body 50 is attachable to the upper container 32 so as to cover the opening 34 and the lower container 22 so as to cover the opening 24.

The lid body 50 includes a lid main body 51 and a rubber layer 56 for providing required air tightness and liquid tightness. The lid body 50 also includes an inlet 52 through which a treatment liquid is poured, a sealing rubber 62, and the second air pressure adjuster 70. Herein, the inlet 52 is composed of an elastomer that fills a circular hole which penetrates through the lid main body 51 and the rubber layer 56 so that a treatment liquid can be poured with a needle bottle (not shown). The sealing rubber 62 is air-tightly and liquid-tightly connected to a cylindrical member 64 disposed so as to penetrate through the upper container 32 in a vertical direction. The sealing rubber 62 and the cylindrical member 64 constitute the first air pressure adjuster 60. The sealing rubber 62 is attached so as to fill a circular hole which penetrates through the lid main body 51 and the rubber layer 56. The insertion with a needle member 66 (e.g., refer to FIG. 5(c)) allows circulation of the outside air and the gas in the collection chamber 20 and the removal of the needle member 66 allows the interruption of the circulation of the outside air and the gas in the collection chamber 20 due to resilience of the elastomer. In the sealing rubber 62, the circulation and the interruption of the circulation can be achieved not only by inserting and removing the needle member 66 but also by opening and closing a valve 68 connected to the needle member 66. The second air pressure adjuster 70 is obtained by filling a circular hole which penetrates through the lid main body 51 and the rubber layer 56 with a material having air permeability and liquid impermeability, which always allows circulation of gas. Since the circulation of the outside air and the gas in the tissue holding chamber 30 is always achieved, the air pressure in the tissue holding chamber 30 is always equal to that of the outside air. The material having air permeability and liquid impermeability is not particularly limited and may be a fluorocarbon resin such as polytetrafluoroethylene or a silicon resin. The material may be a solid body or may have micropores (e.g., pores with a diameter of several to several tens of micrometers) formed therein.

Figure 4:
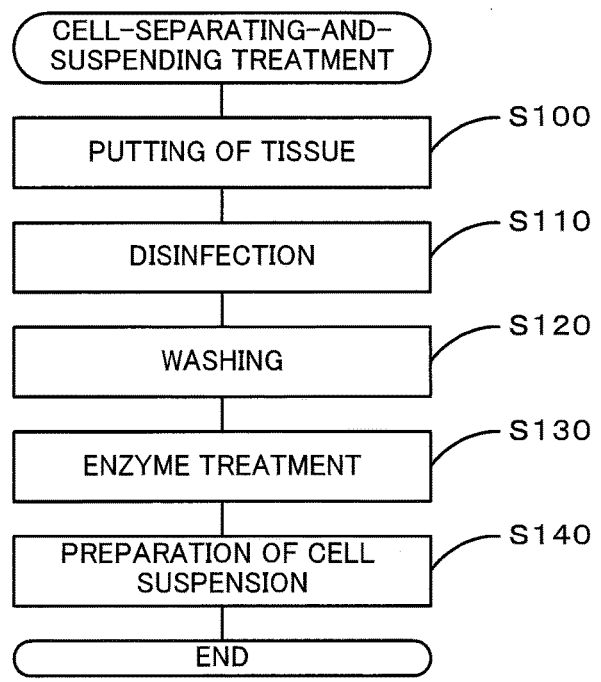
FIG. 4 is a flowchart showing processes of a cell-separating-and-suspending treatment.

Next, a specific method for separating a cell from a tissue and preparing a cell suspension using the cell separation container according to the first embodiment will be described. FIG. 4 is a flowchart showing processes of a cell-separating-and-suspending treatment. This treatment is started while the lower container 22 and the upper container 32 are attached to each other and the lid body 50 is not attached thereto.

In the cell-separating-and-suspending treatment, first, a tissue is put into the tissue holding chamber 30 of the cell separation container 10 through the opening 34 (Step S100). By pouring a transport liquid into the tissue holding chamber 30 after the tissue is put, the cell separation container can also be used as a transport container. In this case, when the transport liquid is poured through the inlet 52 after the lid body 50 is attached, the collection chamber 20 is hermetically sealed due to the transport liquid serving as a lid. Therefore, the transport liquid is held in the tissue holding chamber 30 together with the tissue by the above-described upward supporting force. Thus, transport can be performed while the tissue is immersed in the transport liquid in the tissue holding chamber 30. When the cell separation container is used as such a transport container, the cell-separating-and-suspending treatment can be performed using the cell separation container itself after the transport. The transport liquid may be appropriately determined in accordance with a tissue to be transported. Examples of the transport liquid include a phosphate buffer solution (PBS), a Ringer's solution, and a culture medium.

Figure 5:
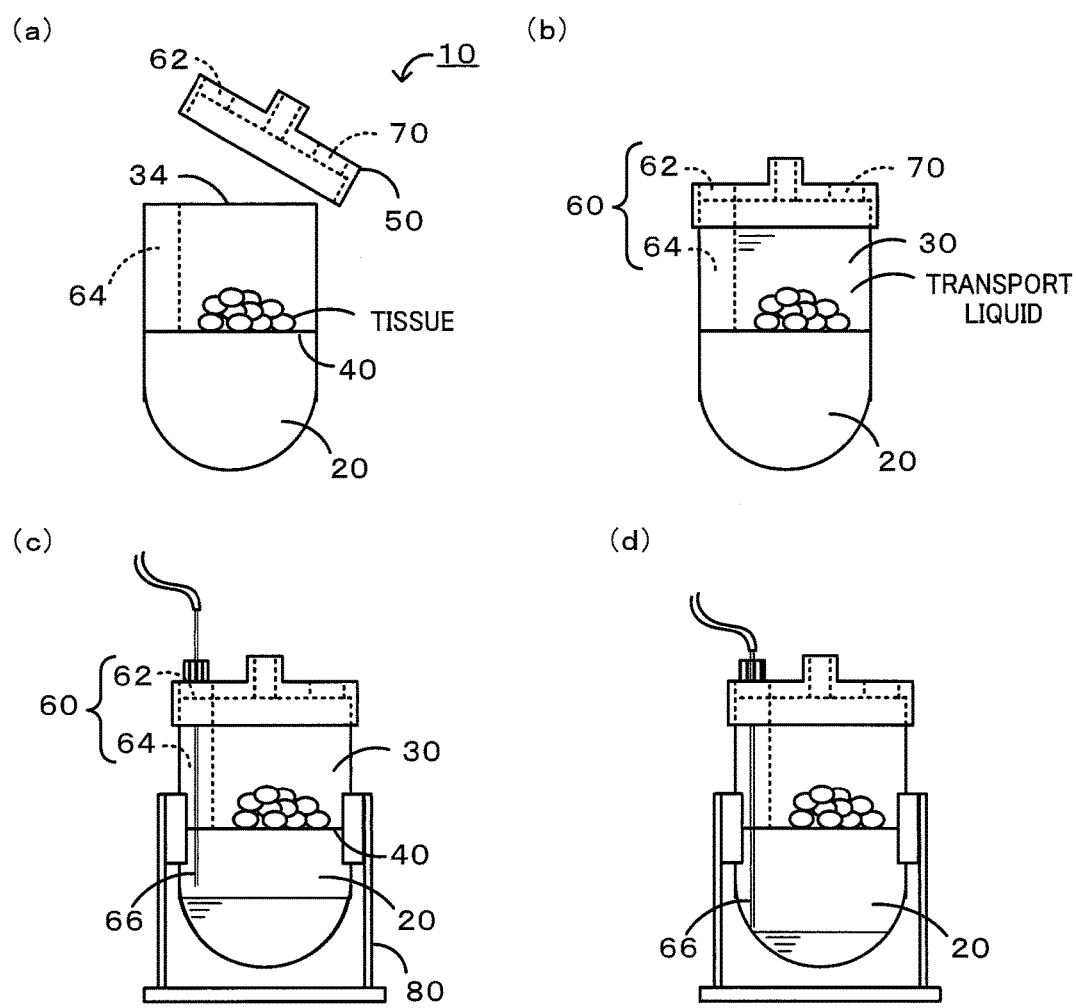
FIG. 5 includes schematic views showing putting and ejection of a tissue and a transport liquid.

FIG. 5 includes schematic views showing the putting of the tissue and the transport liquid and the ejection of the transport liquid. FIG. 5(a) shows a state in which the tissue has been put. FIG. 5(b) shows a state before the transport liquid is ejected. In FIG. 5(b), the first air pressure adjuster 60 is in a state of allowing the interruption of gas circulation and the second air pressure adjuster 70 is in a state of allowing gas circulation. Therefore, the collection chamber 20 connected to the first air pressure adjuster 60 is hermetically sealed because of the transport liquid serving as a lid. Consequently, the put tissue and transport liquid are held in the tissue holding chamber 30 by the upward supporting force without being ejected to the collection chamber 20 side.

Subsequently, as shown in FIG. 5(c), when the needle member 66 is made to penetrate through the sealing rubber 62 of the first air pressure adjuster 60, the collection chamber 20 is ventilated with the outside air and thus the gas in the collection chamber 20 can flow out. This decreases the upward supporting force and the transport liquid held in the tissue holding chamber 30 is ejected to the collection chamber 20 side by gravity. Herein, since the tissue is larger than the pore size of the filter 40, the tissue is held in the tissue holding chamber 30 without passing through the filter 40. An aspirator (not shown) is then connected to the needle member 66 to eject the transport liquid in the collection chamber 20 under suction (refer to FIG. 5(d)). Each of the operations may be performed while the cell separation container 10 is appropriately inclined or may be performed while the cell separation container 10 is fixed using a holder 80 as shown in FIGS. 5(c) and 5(d). The same applies to the following operations.

Figure 6:
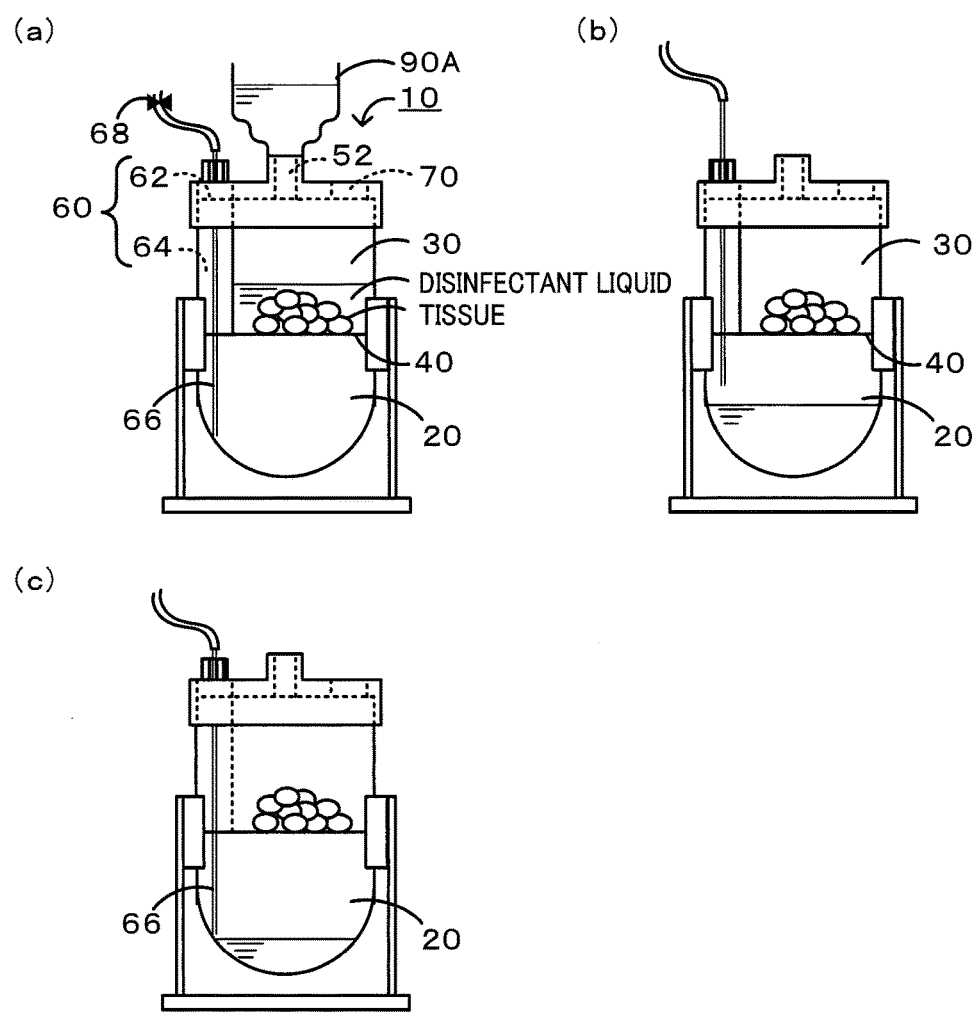
FIG. 6 includes schematic views showing disinfection of the tissue.

Subsequently, the tissue held in the tissue holding chamber 30 is disinfected (Step S110). FIG. 6 includes schematic views showing the disinfection of the tissue. In the case where the tissue is transported using a different container, this process can be performed immediately after the putting of the tissue (Step S100 in FIG. 5(a)). A disinfectant liquid may be determined in view of, for example, the disinfecting effect on the tissue and the influence on the cell. Examples of the disinfectant liquid include alcohols and a povidone-iodine solution. In the disinfection, first, the valve 68 connected to the needle member 66 is closed. Then, a needle of a needle bottle 90A containing the disinfectant liquid is made to penetrate through the inlet 52 to pour the disinfectant liquid into the tissue holding chamber 30 (refer to FIG.

6(a)). Herein, the first air pressure adjuster 60 is in a state of allowing the interruption of gas circulation because the valve 68 connected to the needle member 66 is closed, and the second air pressure adjuster 70 is in a state of allowing gas circulation. Therefore, the collection chamber 20 to which the first air pressure adjuster 60 is connected is hermetically sealed due to the disinfectant liquid serving as a lid. Consequently, the disinfectant liquid is held in the tissue holding chamber 30 by the upward supporting force without being ejected to the collection chamber 20 side. Subsequently, by opening the valve 68 connected to the needle member 66, the gas in the collection chamber 20 and the outside air are circulated and thus the gas in the collection chamber 20 can flow out. This decreases the upward supporting force and the disinfectant liquid held in the tissue holding chamber 30 is ejected to the collection chamber 20 side as shown in FIG. 6(b). Herein, since the tissue is larger than the pore size of the filter 40, the tissue is held in the tissue holding chamber 30 without passing through the filter 40. An aspirator (not shown) is then connected to the needle member 66 to eject the disinfectant liquid in the collection chamber 20 under suction (refer to FIG. 6(c)).

Subsequently, the tissue held in the tissue holding chamber 30 is washed (Step S120). A washing liquid may be determined in view of, for example, the washing effect and the influence on the cell. Examples of the washing liquid include a phosphate buffer solution (PBS), a Ringer's solution, and a physiological saline solution. The number of times of the washing may be freely set, but is desirably, for example, about twice. The specific operations are the same as those in Step S110, except for use of the washing liquid instead of the disinfectant liquid. Therefore, the description is omitted. If this process is performed multiple times, the same operations may be repeatedly performed.

Figure 7:
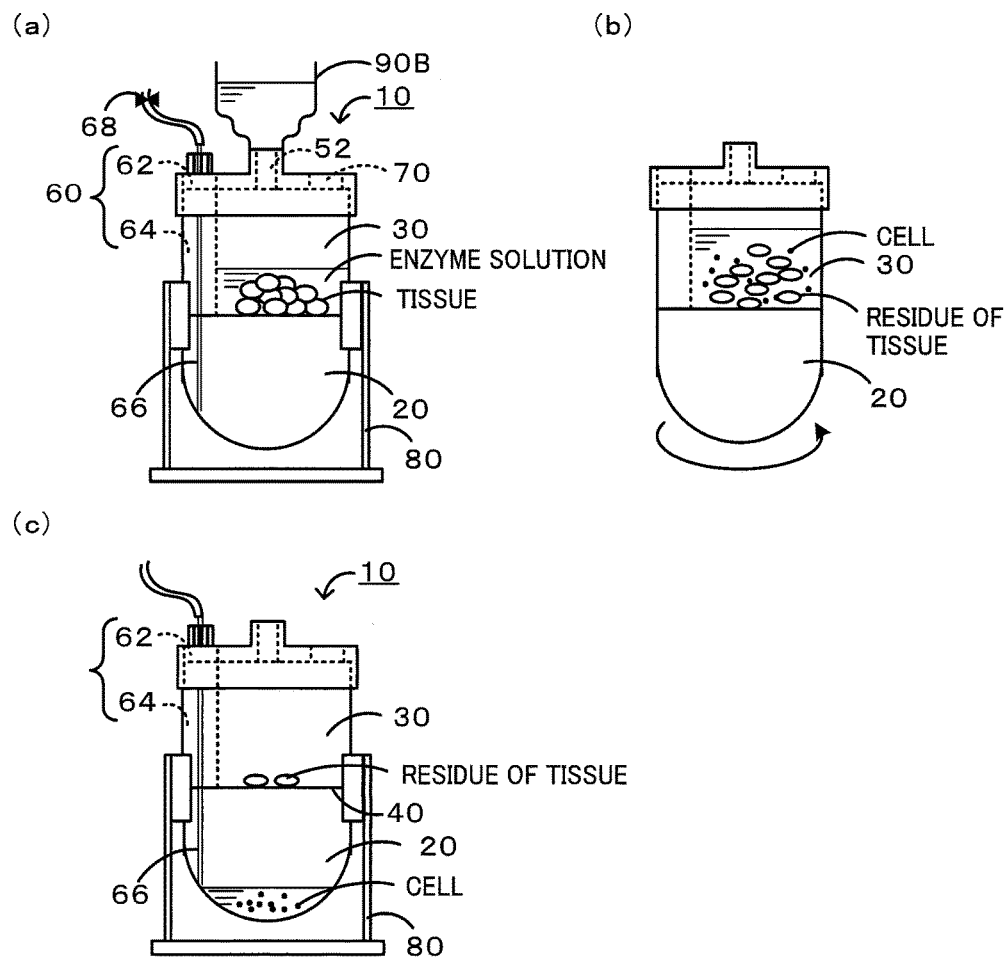
FIG. 7 includes schematic views showing an enzyme treatment.

Subsequently, an enzyme treatment is performed with an enzyme solution in order to separate a cell from the tissue held in the tissue holding chamber 30 (Step S130). FIG. 7 includes schematic views showing an enzyme treatment. The enzyme solution may be determined in accordance with the tissue to be treated. For example, a trypsin solution is used when the tissue is a skin tissue and a collagenase solution is used when the tissue is a cartilage tissue. In the enzyme treatment, the valve 68 connected to the needle member 66 is closed. Then, a needle of a needle bottle 90B containing the enzyme solution is made to penetrate through the inlet 52 to pour the enzyme solution into the tissue holding chamber 30 (refer to FIG. 7(a)). In this case, the enzyme solution is also held in the tissue holding chamber 30 without being ejected to the collection chamber 20 side as in the case of the disinfectant liquid.

In this state, the enzyme solution is left to stand for a predetermined time (for example, one hour or three hours). Consequently, an enzyme reaction proceeds in the tissue holding chamber 30 and a cell can be separated from the tissue. Herein, after the needle member 66 is removed from the first air pressure adjuster 60 and the cell separation container 10 is detached from the holder 80, the enzyme reaction using the enzyme solution may be facilitated by rotary shaking as shown in FIG. 7(b). The rotary shaking conditions may be appropriately set in accordance with the tissue and the enzyme solution. For example, the rotary shaking is performed at 180 rpm for one hour or at 60 rpm for three hours using a rotary shaker. Herein, the first air pressure adjuster 60 is in a state of allowing the interruption of gas circulation because the needle member 66 is removed and the second air pressure adjuster 70 is in a state of allowing gas circulation. Therefore, the gas in the collection chamber 20 to which the first air pressure adjuster 60 is connected is hermetically sealed. The hermetically sealed state of the collection chamber 20 is maintained even if shaking is performed as long as at least a filter surface is not exposed to the gas in the tissue holding chamber 30. Consequently, the enzyme solution is held in the tissue holding chamber 30 without being ejected to the collection chamber 20 side. This effect can be maintained even when the filter surface is momentarily exposed to the gas in the tissue holding chamber 30, though depending on the relationship between the surface tension of the treatment liquid and the pore size of the filter. This allows the rotary shaking to be performed under more vigorous shaking conditions.

Subsequently, as shown in FIG. 7(c), the cell separation container 10 is fixed onto the holder 80 and the needle member 66 is made to penetrate through the sealing rubber 62 of the first air pressure adjuster 60 (in the case where the enzyme treatment is performed in a standing manner, the valve 68 connected to the needle member 66 is opened). In this case, the enzyme solution held in the tissue holding chamber 30 is also ejected to the collection chamber 20 side as in the case of the disinfectant liquid. The ejected enzyme solution contains a cell that is separated from the tissue as a result of the enzyme treatment and that has a size smaller than the pore size of the filter 40. For example, a residue of the tissue having a size larger than the pore size of the filter 40 is held in the tissue holding chamber 30 without passing through the filter 40.

The enzyme treatment may be appropriately set in accordance with the state of the cell separation process from the tissue. For example, the enzyme solution may be changed or the enzyme treatment may be repeatedly performed.

Figure 8:
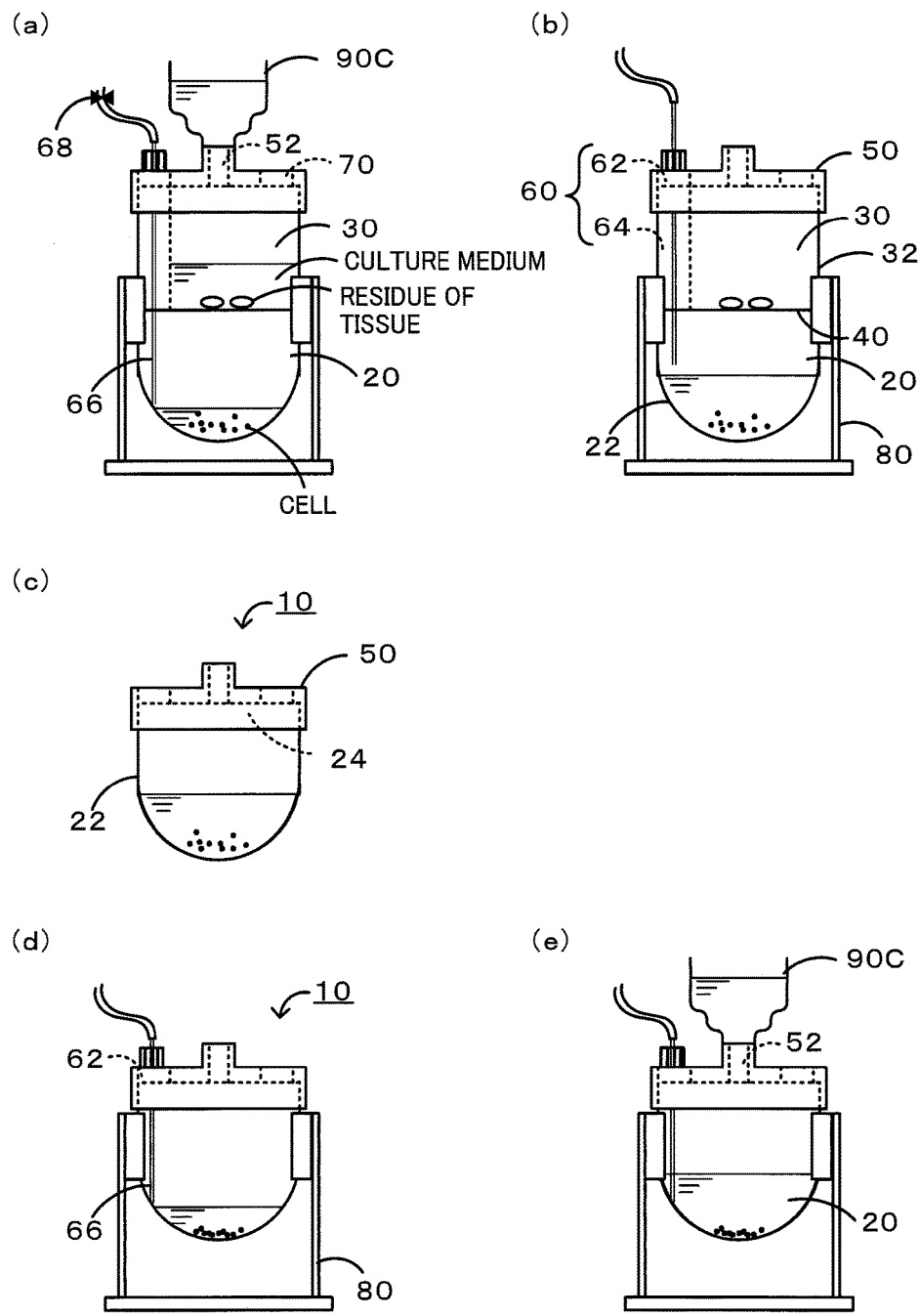
FIG. 8 includes schematic views showing a cell suspension treatment.

Subsequently, a suspension treatment is performed in which a cell suspension is prepared by adding a culture medium to the cell ejected to the collection chamber 20 side (Step S140). FIG. 8 includes schematic views showing a cell suspension treatment. In the cell suspension treatment, a needle of a needle bottle 90C containing a culture medium is made to penetrate through the inlet 52 to pour the culture medium into the tissue holding chamber 30 while the valve 68 connected to the needle member 66 is closed (refer to FIG. 8(a)). The type of culture medium used herein may be appropriately selected in accordance with, for example, the type of separated cell and whether the enzyme reaction stops or not. A desired culture medium is, for example, an FBS-containing DMEM. In this case, the culture medium is also held in the tissue holding chamber 30 without being ejected to the collection chamber 20 side as in the case of the disinfectant liquid. Subsequently, when the valve 68 connected to the needle member 66 is opened, the gas in the collection chamber 20 can flow out. This decreases the upward supporting force and the culture medium held in the tissue holding chamber 30 is ejected to the collection chamber 20 side as shown in FIG. 8(b). Herein, since the residue of the tissue is larger than the pore size of the filter 40, the residue of the tissue is still held in the tissue holding chamber 30 without passing through the filter 40 and a cell left in the residue or the like is ejected to the collection chamber 20 side together with the culture medium. Subsequently, the needle member 66 is removed from the first air pressure adjuster 60 and the cell separation container 10 is detached from the holder 80. After the lower container 22, the upper container 32, and the lid body 50 are detached from each other, the lid body 50 is attached to the lower container 22 so as to cover the opening 24 of the lower container 22 as shown in FIG. 8(c). The downsized cell separation container 10 is subjected to centrifugal separation to aggregate the cell into a cell pellet in a lower portion of the lower container 22, and thus the cell pellet is separated from the treatment liquid (in this case, a mixed liquid of the enzyme solution and the culture medium). The centrifugal separation is performed, for example, at 1500 rpm for about 5 minutes. The centrifugal separation may be performed without detaching the lower container 22 and the upper container 32. Subsequently, as shown in FIG. 8(d), the cell separation container 10 is fixed onto the holder 80, the needle member 66 is made to penetrate through the sealing rubber 62 and connected to an aspirator (not shown), and the treatment liquid is carefully aspirated without aspirating the cell pellet. A needle of the needle bottle 90C containing a culture medium is then made to penetrate through the inlet 52 to pour the culture medium into the collection chamber 20 (refer to FIG. 8(e)). After that, for example, the container is shaken or pipetting is performed by pipetting up and down through the needle member 66 to prepare a cell suspension. After the preparation of the cell suspension, the operations shown in FIGS. 8(c) to 8(e) may be repeatedly performed if required. The preparation of the cell suspension may include a process of incorporating a predetermined amount of cell into a predetermined amount of suspension by counting the number of cells. In FIGS. 5 to 8 used in the description, the needle member 66, the treatment liquids, the tissue, the residue of the tissue, and the cell should be each indicated by a broken line, but are each indicated by a solid line for convenience.

According to the cell separation container 10 of the first embodiment described above, when the tissue is treated with the treatment liquid, the circulation of the gas in the collection chamber 20 and the outside air is interrupted to prevent the inflow and outflow of gas. Consequently, the upward supporting force is maintained and the treatment liquid is held in the tissue holding chamber 30, which allows a treatment performed in the tissue holding chamber 30. When the treatment with the treatment liquid is completed, the gas in the collection chamber 20 is made to communicate with the outside to allow the inflow and outflow of the gas. This decreases the upward supporting force and thus the treatment liquid is ejected to the collection chamber. As a result, the treatment liquid can be separated from the tissue held in the tissue holding chamber 30 and can be ejected. A series of operations for treating a tissue with a treatment liquid and separating a cell from the tissue can be easily performed efficiently. Furthermore, since the treatment with the treatment liquid is completed in the tissue holding chamber 30, the entire cell separation container 10 is not necessarily filled with the treatment liquid. This can decrease the amount of the treatment liquid used. Furthermore, the cell separation container 10 includes the first air pressure adjuster 60 that allows the circulation of the gas in the collection chamber 20 and the outside air and the interruption of the circulation and the second air pressure adjuster 70 that always allows the circulation of the gas in the tissue holding chamber 30 and the outside air. Therefore, the inflow and outflow of the gases in the collection chamber 20 and the tissue holding chamber 30 can be easily controlled with a simple structure. Furthermore, the first air pressure adjuster 60 also has a function as an outlet for ejecting the treatment liquid and the cell in the collection chamber 20, and thus an additional outlet is not required and a simple structure can be employed. Furthermore, the cell separation container 10 includes the lower container 22 having the opening 24 in the upper portion thereof; the upper container 32 that has the opening 34 in the upper portion thereof, includes the filter 40 in the bottom portion thereof, and is connected to the lower container 22 in the lower portion thereof; and the lid body 50 attachable to the upper container 32 so as to cover the opening 34 of the upper container 32. The lower container 22 has a structure to which the lid body 50 is attachable. Therefore, the upper container 32 is detached and the lid body 50 is directly attached to the lower container 22 after the completion of cell separation, which can decrease the size of the cell separation container 10 when a suspension is prepared from the separated cell or during the storage.

Second Embodiment

Figure 9:
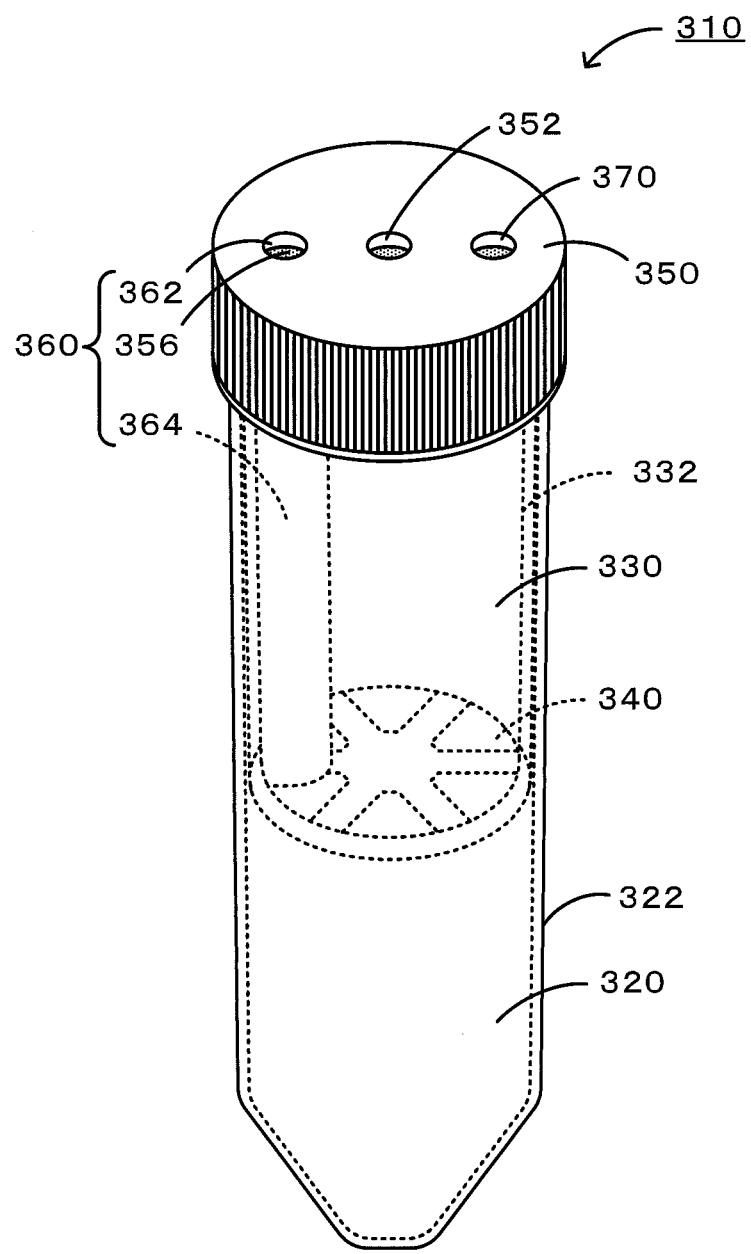
FIG. 9 is a perspective view of a cell separation container 310 according to a second embodiment.
Figure 10:
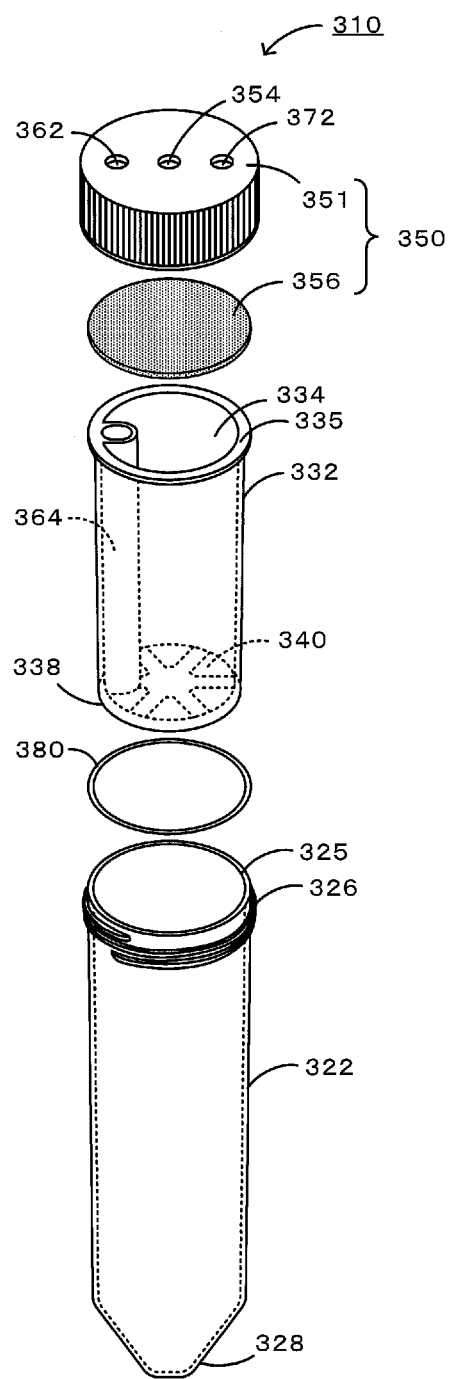
FIG. 10 is a perspective view of the cell separation container 310 before assembling.

FIG. 9 is a perspective view of a cell separation container 310 according to a second embodiment. FIG. 10 is a perspective view of the cell separation container 310 before assembling.

As shown in FIG. 9, the cell separation container 310 includes a collection chamber 320 and a tissue holding chamber 330 which are partitioned by a filter 340. The cell separation container 310 includes a first air pressure adjuster 360 configured to adjust the inflow and outflow of gas in the collection chamber 320 and a second air pressure adjuster 370 configured to adjust the inflow and outflow of gas in the tissue holding chamber 330. Thus, the inflow and outflow of the outside air and the gases in the collection chamber 320 and the tissue holding chamber 330 can be adjusted. As shown in FIG. 10, the cell separation container 310 includes an outer container 322, an inner container 332 incorporated into an upper portion of the outer container 322, and a lid body 350 attachable to an outer container 322 into which the inner container 332 has been incorporated. In this case, a region surrounded by the outer container 322 and the lid body 350 and located outside the inner container 332 serves as the collection chamber 320. A region surrounded by the inner container 332 and the lid body 350 serves as the tissue holding chamber 330.

The same container as the lower container 22 can be used as the outer container 322, and therefore the description of the outer container 322 is omitted herein.

The inner container 332 has a cylindrical shape and has an opening 334 in the upper portion thereof. The inner container 332 includes a flange 335 at the upper end thereof, a filter 340 disposed in a bottom portion 338 thereof, and a cylindrical member 364 disposed so as to penetrate through the inner container 332 in a vertical direction. The same filter as the filter 40 can be used as the filter 340, and therefore the description of the filter 340 is omitted herein. When the inner container 332 is inserted into the outer container 322, the flange 335 is hooked onto an upper end surface 325 of the outer container 322. Thus, the inner container 332 is incorporated into an upper portion of the outer container 322 while a certain distance is kept between the inner container 332 and the a bottom portion 328 of the outer container 322. An O ring 380 lies in a portion between the upper end surface 325 of the outer container 322 and the flange 335 of the inner container 332 so that leakage of liquid and gas from the portion can be prevented. The O ring 380 preferably has a rubber hardness of, for example, about 40 to 50. The O ring 380 is made of, for example, silicone rubber.

The lid body 350 includes a lid main body 351 and a rubber layer 356. The lid main body 351 includes an internal thread (not shown) at the internal circumference thereof. The internal thread and an external thread 326 of the outer container 322 are screwed so that the lid body 350 and the outer container 322 are connected to each other. The lid main body 351 includes through-holes 354, 362, and 372 formed therein. The lid main body 351 and the rubber layer 356 are in close contact with each other. The through-hole 354 and the rubber layer 356 constitute an inlet 352. The through-hole 362, the rubber layer 356, and the cylindrical member 364 constitute a first air pressure adjuster 360. The through-hole 372 and the rubber layer 356 constitute a second air pressure adjuster 370. Through the rubber layer 356 serving as part of the inlet 352, a treatment liquid can be poured using a needle bottle (not shown). In the rubber layer 356 serving as part of the first air pressure adjuster 360, the circulation of gas in the collection chamber 320 and the outside air can be achieved by causing a needle member to penetrate through the rubber layer 356, and the circulation can be interrupted by resilience of rubber generated when the needle member is removed. In the rubber layer 356 serving as part of the second air pressure adjuster 370, the circulation of gas in the tissue holding chamber 330 and the outside air can be achieved by causing a needle member to penetrate through the rubber layer 356, and the circulation can be interrupted by resilience of rubber generated when the needle member is removed. A surface of the rubber layer 356 that is in contact with the lid main body 351 is made of a material having a high rubber hardness (e.g., a rubber hardness of 70 to 90) (in conformity with Type A Durometer Hardness in JIS K 6253, the same shall apply hereinafter). A surface of the rubber layer 356 that is in contact with the outer container 322 and/or the inner container 332 is made of a material having a low rubber hardness (e.g., a rubber hardness of 20 to 50). The rubber layer 356 is preferably made of a material through which, for example, a needle member and a needle of a needle bottle are easily made to penetrate. For example, silicone rubber is suitably used.

A method for preparing a cell suspension by separating a cell from a tissue using the cell separation container according to the second embodiment can be performed in conformity with the method in the first embodiment, and therefore the description of the method is omitted herein.

According to the cell separation container 310 of the second embodiment described above, when the tissue is treated with the treatment liquid, the circulation of the gas in the collection chamber 320 and the outside air is interrupted to prevent the inflow and outflow of gas. Consequently, the upward supporting force is maintained and the treatment liquid is held in the tissue holding chamber 330, which allows a treatment performed in the tissue holding chamber 330. When the treatment with the treatment liquid is completed, the needle member or the like is inserted into the second air pressure adjuster 370 to cause the gas in the tissue holding chamber 330 to freely flow in or flow out while at the same time the gas in the collection chamber 320 is made to communicate with the outside to allow the inflow and outflow of the gas. This decreases the upward supporting force and thus the treatment liquid is ejected to the collection chamber 320. As a result, the treatment liquid can be separated from the tissue held in the tissue holding chamber 330 and can be ejected. A series of operations for treating a tissue with a treatment liquid and separating a cell from the tissue can be easily performed efficiently. Furthermore, since the treatment with the treatment liquid is completed in the tissue holding chamber 330, the entire cell separation container 310 is not necessarily filled with the treatment liquid. This can decrease the amount of the treatment liquid used. Furthermore, the cell separation container 310 includes the first air pressure adjuster 360 that allows the circulation of the gas in the collection chamber 20 and the outside air and the interruption of the circulation, and the second air pressure adjuster 370 that allows the circulation of the gas in the tissue holding chamber 330 and the outside air and the interruption of the circulation. Therefore, the inflow and outflow of the gases in the collection chamber 320 and the tissue holding chamber 330 can be easily controlled with a simple structure. Furthermore, the first air pressure adjuster 360 also has a function as an outlet for ejecting the treatment liquid and the cell in the collection chamber 320, and thus an additional outlet is not required and a simple structure can be employed. Furthermore, the cell separation container 310 has high versatility because a commercially available centrifuge tube or the like can be applied to the outer container 322 and the lid body 350. Furthermore, the rubber layer 356 partly functions as the inlet 352, the first air pressure adjuster 360, and the second air pressure adjuster 370. Therefore, there is no need to separately prepare the elastomer for the inlet 52, the sealing rubber 62 for the first air pressure adjuster 60, and the material having air permeability and liquid impermeability for the second air pressure adjuster 70, which are used in the first embodiment. Furthermore, the rubber hardness of a surface of the rubber layer 356 that is in contact with the lid main body 351 is higher than that of a surface of the rubber layer 356 that is in contact with the outer container 322 and/or the inner container 332. In this case, a friction is not easily produced between the rubber layer 356 and the lid main body 351 and thus the rubber layer 356 is easily brought into close contact with the outer container 322 and the inner container 332. Therefore, when the lid body 350 is attached to the outer container 322, the rubber layer 356 is not easily twisted and thus the lid is not easily unscrewed. Consequently, the air tightness of the outer container 322 and the inner container 332 can be further improved.

Other Embodiments

The present invention is not limited to the above embodiments and various modifications can be made without departing from the technical scope of the present invention.

Figure 11:
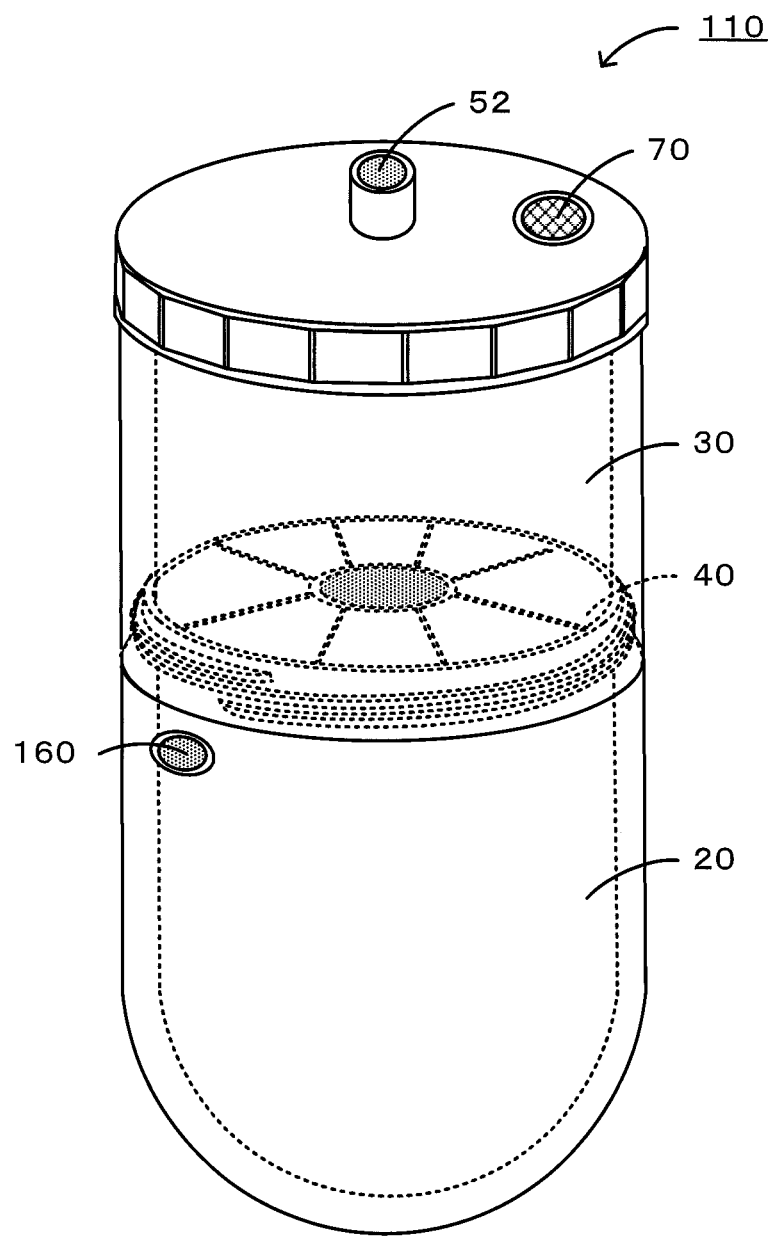
FIG. 11 shows a cell separation container in one modified structure.

For example, it has been described in the first embodiment that the first air pressure adjuster 60 is constituted by the sealing rubber 62 disposed in the lid body 50 and the cylindrical member 64 disposed so as to penetrate through the upper container 32, but the first air pressure adjuster 60 may be disposed, for example, on a side wall of the lower container 22. FIG. 11 shows such a structure (modification). A cell separation container 110 shown in FIG. 11 is the same as the cell separation container 10 shown in FIG. 1, except that a first air pressure adjuster 160 is disposed on a side wall of the lower container 22. Therefore, the same reference numerals are given and the detailed description is omitted.

It has been described in the first embodiment that the sealing rubber 62 that serves as part of the first air pressure adjuster 60 is composed of an elastomer, and the insertion with the needle member 66 allows circulation of the outside air and the gas in the collection chamber 20 and the removal of the needle member 66 allows the interruption of the circulation due to resilience of the elastomer, but such a structure is not limited thereto. For example, a lid that can be opened and closed or a valve that can be opened and closed may be disposed. Alternatively, a shape of luer-lock fittings or tube connectors may be employed. This also applies to the second embodiment. In addition to the sealing rubber 62 in the first embodiment and the rubber layer 356 in the second embodiment, the lid that can be opened and closed and the valve that can be opened and closed correspond to a sealing member of the present invention.

It has been described in the first embodiment that the second air pressure adjuster 70 is made of a material having air permeability and liquid impermeability, which always allows circulation of gases, but the second air pressure adjuster 70 is not limited thereto. For example, the second air pressure adjuster 70 may be composed of an elastomer used for the sealing rubber 62 so as to interrupt the circulation of gases during transport or the like. A lid that can be opened and closed or a valve that can be opened and closed may be disposed. Alternatively, a shape of luer-lock fittings or tube connectors may be employed. The same also applies to the second embodiment.

It has been described in the first and second embodiments that the air pressure adjusters are disposed for both the collection chambers 20 and 320 and the tissue holding chambers 30 and 330, but the air pressure adjuster may be disposed for one of them. For example, a pressure-reducing device such as a vacuum pump may be disposed for the collection chambers 20 and 320 as the air pressure adjuster. When the pressure-reducing device is not operated, the treatment liquid is held in the tissue holding chambers 30 and 330. When the pressure-reducing device is operated to control the air pressure of the collection chambers 20 and 320 to be lower than that of the tissue holding chambers 30 and 330, the treatment liquid can be ejected from the tissue holding chambers 30 and 330 to the collection chambers 20 and 320. In this case, there is no need to dispose the air pressure adjuster for the tissue holding chambers 30 and 330. Alternatively, for example, a pressurizing device such as a pressurized cylinder may be disposed for the tissue holding chambers 30 and 330 as the air pressure adjuster. When the pressurizing device is not operated, the treatment liquid is held in the tissue holding chambers 30 and 330. When the pressurizing device is operated to control the air pressure of the tissue holding chambers 30 and 330 to be higher than that of the collection chambers 20 and 320, the treatment liquid can be ejected from the tissue holding chambers 30 and 330 to the collection chambers 20 and 320. In this case, there is no need to dispose the air pressure adjuster for the collection chambers 20 and 320. Even when the air pressure adjusters are disposed for both the collection chambers 20 and 320 and the tissue holding chambers 30 and 330, the pressure-reducing device or the pressurizing device may be suitably employed as the air pressure adjuster.

It has been described in the first embodiment that the upper container 32 is formed by integrating the cylindrical part and the filter 40, but the upper container 32 is not limited thereto. For example, the upper container 32 may include an outer frame body that has openings in the upper and lower portions thereof and is connected to the lower container in the lower portion thereof and an incorporation body that includes a filter and is detachably incorporated into the outer frame body. Thus, a desired operation can be performed by changing the combination of the outer frame body and the incorporation body. In this case, for example, the upper container 32 may include a cylindrical outer frame body and an incorporation body having a cylindrical shape with a bottom at which a filter is heat-sealed, wherein the inner circumference of the outer frame body and the outer periphery of the incorporation body are in close contact with each other in an air-tight and liquid-tight manner. Alternatively, the upper container 32 may include a cylindrical outer frame body including a gasket that can fix a filter at a lower end and an incorporation body which is the filter itself, wherein the cylindrical outer frame body and the incorporation body are in close contact with each other in an air-tight and liquid-tight manner by incorporating the incorporation body into the outer frame body so that the incorporation body is brought into close contact with the gasket. It has also been described in the second embodiment that the inner container 332 is formed by integrating the cylindrical part and the filter 340, but the inner container 332 is not limited thereto. For example, the inner container 332 may include a cylindrical outer frame body including a gasket that can fix a filter at a lower end and an incorporation body which is the filter itself, wherein the incorporation body is incorporated into the outer frame body so as to be brought into close contact with the gasket.

It has been described in the first embodiment that the inlet 52 is composed of an elastomer that fills a circular hole which penetrates through the lid main body 51 and the rubber layer 56 so that a treatment liquid can be poured with a needle bottle (not shown), but the inlet 52 is not limited thereto. For example, the inlet 52 may include a lid that can be opened and closed. Alternatively, a shape of luer-lock fittings or tube connectors may be employed. The same also applies to the second embodiment.

Figure 12:
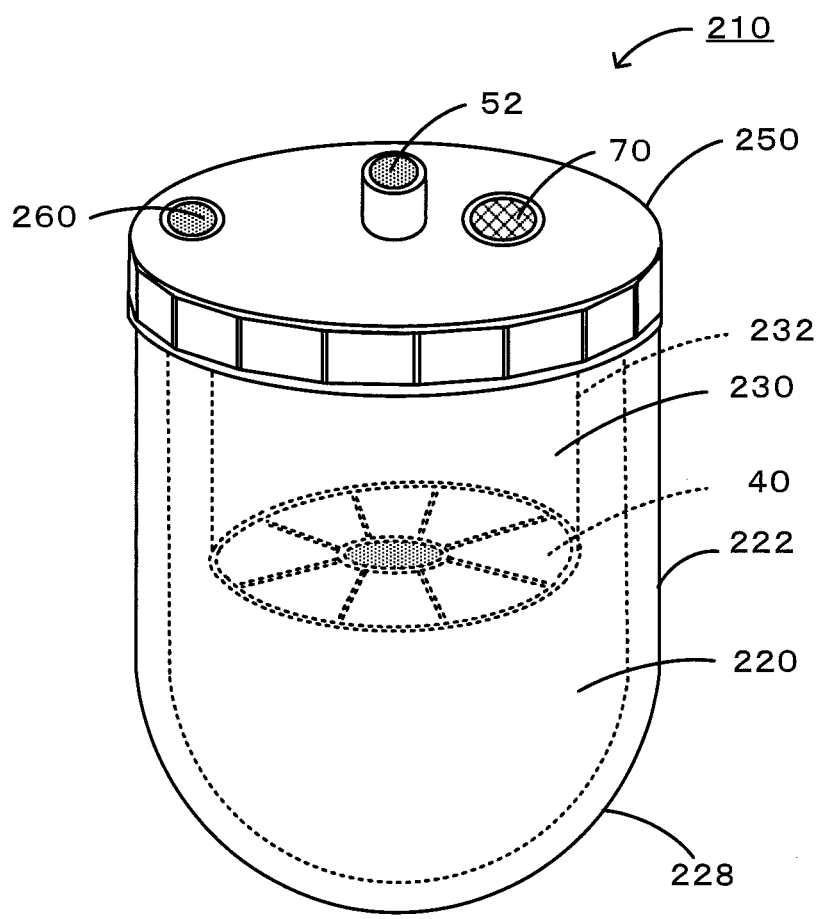
FIG. 12 shows a cell separation container in another modified structure.

It has been described in the first embodiment that the cell separation container 10 includes the lower container 22, the upper container 32, and the lid body 50, but the cell separation container 10 is not limited thereto. For example, as shown in FIG. 12, a cell separation container 210 may include an outer container 222 having an opening in the upper portion thereof; an inner container 232 that is disposed inside the outer container 222 and in an upper portion of the outer container 222, has an opening in the upper portion thereof, and includes the filter 40 disposed in the lower portion thereof; and a lid body 250 attachable to both the outer container 222 and the inner container 232. In the cell separation container 210, a region surrounded by the outer container 222 and the lid body 250 and located outside the inner container 232 serves as a collection chamber 220 and a region surrounded by the inner container 232 and the lid body 250 serves as a tissue holding chamber 230. In this case, the lid body 250 and the inner container 232 can each have a thread so as to be screwed. Herein, the filter 40, the inlet 52, and the second air pressure adjuster 70 are the same as those of the cell separation container 10 shown in FIG. 1, and thus the description thereof is omitted. In the cell separation container 210, a first air pressure adjuster 260 disposed in the lid body 250 is composed of an elastomer. The insertion with a needle member 66 allows circulation of the outside air and the gas in the collection chamber 220 and the removal of the needle member 66 allows the interruption of the circulation due to resilience of the elastomer. The first air pressure adjuster 260 may be disposed, for example, on a side wall of the outer container 222.

Figure 13:
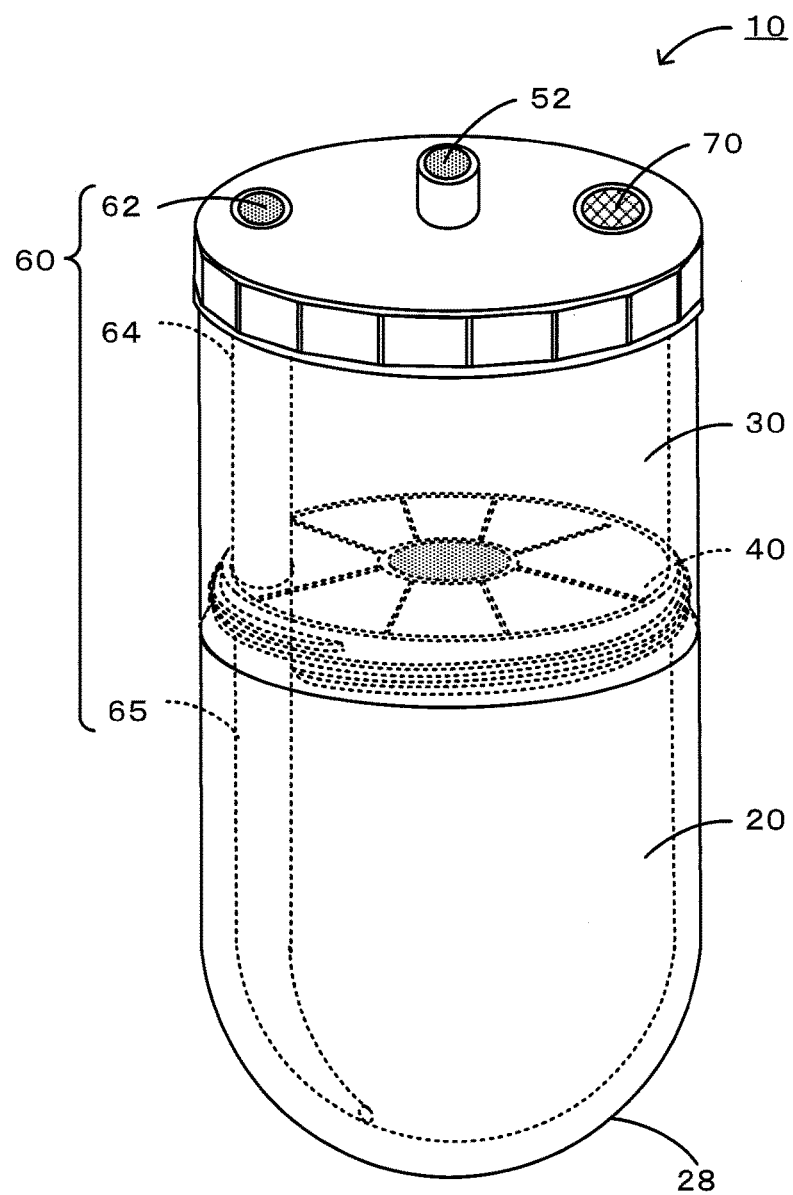
FIG. 13 shows a cell separation container in another modified structure.

It has been described in the first embodiment that the needle member 66 that has penetrated through the sealing rubber 62 of the first air pressure adjuster 60 is connected to an aspirator to eject the treatment liquid and the cell in the collection chamber 20 under suction, but such a structure is not limited thereto. For example, an additional outlet that can be opened and closed may be disposed on the collection chamber 20. As shown in FIG. 13, an aspirating tube 65 that extends from the cylindrical member 64 and reaches the bottom portion 28 of the lower container 22 may be disposed and an aspirator or the like may be directly connected to the first air pressure adjuster 60 to eject the treatment liquid and the cell in the collection chamber 20 under suction. Such a structure is suitable for automation or the like because an operation for, for example, inserting the needle member 66 into the lower container 22 so as to reach the bottom portion 28 can be omitted. This also applies to the second embodiment. An outlet for ejecting the treatment liquid and the cell in the collection chamber 320 under suction may be additionally disposed on the collection chamber 320 or an aspirating tube that extends from the cylindrical member 364 and reaches the bottom portion 328 of the outer container 322 may be disposed.

In the first embodiment, the lid body 50 is used, but a lid body having a structure of the lid body 350 in the second embodiment may be used instead of the lid body 50. In the second embodiment, the lid body 350 is used, but a lid body having a structure of the lid body 50 in the first embodiment may be used instead of the lid body 350.

In the second embodiment, the O ring 380 is used, but such an O ring is not necessarily used as long as required air tightness and liquid tightness can be achieved. It has been described in the second embodiment that the inner container 332 includes the cylindrical member 364 disposed so as to penetrate through the inner container 332 in a vertical direction, but the inner container 332 is not limited thereto. For example, the inner container 332 may include a groove portion on a side wall of the inner container 332, the groove portion extending in a vertical direction.

The present application claims priority from Japanese Patent Application No. 2012-000138 filed on Jan. 4, 2012, the entire contents of which are incorporated herein by reference.

INDUSTRIAL APPLICABILITY

The present invention is applicable in cell culture techniques of culturing cells in vitro.

The invention claimed is:

1. A cell separation container that separates a cell from a tissue using a treatment liquid, the cell separation container comprising:
    a collection chamber for collecting at least one of the treatment liquid and the cell;
    a tissue holding chamber disposed above the collection chamber and including a pouring inlet through which the treatment liquid is poured;
    a disc-shaped filter disposed as the entirety or part of a structure for partitioning the collection chamber and the tissue holding chamber from each other, the filter being capable of holding the tissue and allowing the cell to pass therethrough; and
    an air pressure adjusting mechanism capable of switching between a process of holding a treatment liquid poured into the tissue holding chamber without causing the treatment liquid to pass through the filter and a process of ejecting a treatment liquid poured into the tissue holding chamber to the collection chamber by causing the treatment liquid to pass through the filter, the switching being achieved by adjusting inflow and outflow of gases in the collection chamber and the tissue holding chamber,
    wherein the tissue holding chamber and the collection chamber are configured such that the treatment liquid poured into the tissue holding chamber serves as a lid that hermetically seals the collection chamber, resulting, in the gas in the collection chamber being held in the collection chamber without causing volume change.

2. The cell separation container according to claim 1, wherein the air pressure adjusting mechanism includes a first air pressure adjuster configured to adjust inflow and outflow of the gas in the collection chamber, the first air pressure adjuster being disposed in the collection chamber, and a second air pressure adjuster configured to adjust inflow and outflow of the gas in the tissue holding chamber, the second air pressure adjuster being disposed in the tissue holding chamber.

3. The cell separation container according to claim 2, wherein the first air pressure adjuster allows circulation of the gas in the collection chamber and outside air and interruption of the circulation, and the second air pressure adjuster always allows circulation of the gas in the tissue holding chamber and the outside air.

4. The cell separation container according to claim 1, comprising:
    a lower container having an opening in an upper portion thereof;
    an upper container having an opening in an upper portion thereof, including the filter in a bottom portion thereof, and connected to the lower container in a lower portion thereof; and
    a lid body attachable to the upper container so as to cover the opening of the upper container,
    wherein a region surrounded by the lower container and the bottom portion of the upper container serves as the collection chamber, and a region surrounded by the upper container and the lid body serves as the tissue holding chamber.

5. The cell separation container according to claim 4, wherein the upper container includes an outer frame body having openings in upper and lower portions thereof and connected to the lower container in a lower portion thereof and an incorporation body including the filter and detachably incorporated into the outer frame body.

6. The cell separation container according to claim 4, wherein the lower container has a structure to which the lid body is attachable.

7. The cell separation container according to claim 4, wherein the air pressure adjusting mechanism includes a first air pressure adjuster configured to adjust inflow and outflow of the gas in the collection chamber, the first air pressure adjuster being disposed in the collection chamber, and a second air pressure adjuster configured to adjust inflow and outflow of the gas in the tissue holding chamber, the second air pressure adjuster being disposed in the tissue holding chamber, and
    wherein the first air pressure adjuster includes a sealing member disposed in the lid body and a cylindrical member connected to the sealing member and penetrating through the upper container in a vertical direction.

8. The cell separation container according to claim 7, wherein the first air pressure adjuster includes an aspirating tube that extends from the cylindrical member and reaches a bottom portion of the lower container.

9. The cell separation container according to claim 4, wherein the lid body includes a lid main body that can be attached to and detached from the upper container by screwing and a rubber layer disposed inside the lid main body, and a rubber hardness of a surface of the rubber layer that is in contact with the lid main body is higher than that of a surface of the rubber layer that is in contact with the upper container.

10. The cell separation container according to claim 1, comprising:
    an outer container having an opening in an upper portion thereof;
    an inner container incorporated into an upper portion of the outer container, having an opening in an upper portion thereof, and including the filter in a bottom portion thereof; and
    a lid body attachable to the outer container into which the inner container has been incorporated,
    wherein a region surrounded by the outer container and the lid body and located outside the inner container serves as the collection chamber, and a region surrounded by the inner container and the lid body serves as the tissue holding chamber.

11. The cell separation container according to claim 10, wherein the air pressure adjusting mechanism includes a first air pressure adjuster configured to adjust inflow and outflow of the gas in the collection chamber, the first air pressure adjuster being disposed in the collection chamber, and a second air pressure adjuster configured to adjust inflow and outflow of the gas in the tissue holding chamber, the second air pressure adjuster being disposed in the tissue holding chamber, and
wherein the first air pressure adjuster includes a sealing member disposed in the lid body and a cylindrical member connected to the sealing member and penetrating through the inner container in a vertical direction.

12. The cell separation container according to claim 11, wherein the first air pressure adjuster includes an aspirating tube that extends from the cylindrical member and reaches a bottom portion of the outer container.

13. The cell separation container according to claim 10, wherein the lid body includes a lid main body that can be attached to and detached from the outer container by screwing and a rubber layer disposed inside the lid main body, and a rubber hardness of a surface of the rubber layer that is in contact with the lid main body is higher than that of a surface of the rubber layer that is in contact with the outer container and/or the inner container.

14. The cell separation container according to claim 1, wherein the filter has a pore size of 30 μm or more and 100 μm or less.

15. The cell separation container according to claim 1, wherein the filter has a pore size of 40 μm or more and 70 μm or less.

* * * * *